(12) United States Patent
Drott

(10) Patent No.: US 7,168,334 B1
(45) Date of Patent: Jan. 30, 2007

(54) ARRANGEMENT FOR MEASURING A PROPERTY OF A FLUID PRESENT IN A TUBE

(75) Inventor: Johan Drott, Lund (SE)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/980,066

(22) PCT Filed: May 30, 2000

(86) PCT No.: PCT/SE00/01132

§ 371 (c)(1),
(2), (4) Date: Feb. 27, 2002

(87) PCT Pub. No.: WO00/72747

PCT Pub. Date: Dec. 7, 2000

(51) Int. Cl.
*G01D 21/00* (2006.01)

(52) U.S. Cl. .................... 73/866.5; 73/861; 73/756; 73/209.23; 604/31

(58) Field of Classification Search ............... 604/31, 604/132, 505, 67, 140, 131, 153, 30; 600/310; 73/135, 863.83, 866.5, 86, 37, 861, 23.1, 73/756, 747, 204.23; 804/891.1, 153, 890.1, 804/141–151; 324/138; 373/147
See application file for complete search history.

(56) References Cited

U.S. PATENT DOCUMENTS

| | | | |
|---|---|---|---|
| 4,613,325 A * | 9/1986 | Abrams ........................ 604/65 |
| 4,661,093 A | 4/1987 | Beck et al. | |
| 4,694,834 A | 9/1987 | Meyerhoff et al. | |
| 5,076,108 A * | 12/1991 | Trimarchi ................... 73/866.5 |
| 5,081,866 A * | 1/1992 | Ochiai et al. ............. 73/204.21 |
| 5,676,132 A * | 10/1997 | Tillotson et al. ........ 128/204.23 |
| 5,741,284 A * | 4/1998 | Karlsson ..................... 604/160 |
| 5,951,497 A | 9/1999 | Wallace et al. | |
| 6,117,086 A * | 9/2000 | Shulze ........................ 600/488 |
| 6,240,775 B1 * | 6/2001 | Uramachi et al. ........ 73/204.21 |
| 6,361,206 B1 * | 3/2002 | Bonne ........................ 374/138 |

FOREIGN PATENT DOCUMENTS

| | | |
|---|---|---|
| DE | 35 08 570 A1 | 9/1985 |
| DE | 41 01 549 A1 | 7/1992 |
| EP | 0 413 198 B1 | 2/1991 |
| WO | WO 95/25953 * | 9/1995 |

* cited by examiner

*Primary Examiner*—Kevin C. Sirmons
*Assistant Examiner*—Catherine N. Witczak
(74) *Attorney, Agent, or Firm*—Lerner, David, Littenberg, Krumholtz & Mentlik, LLP

(57) ABSTRACT

Apparatus for measuring a property of a fluid is provided including a tube for retaining the fluid, the tube including a lateral access opening and a domed portion including a sealing surface on the outside wall of the tube surrounding the lateral access opening and a sensor sealingly disposed on the sealing surface surrounding the lateral access opening in the tube for direct contact with the fluid in the tube for sensing the property of the fluid in the tube.

19 Claims, 2 Drawing Sheets

ARRANGEMENT FOR MEASURING A PROPERTY OF A FLUID PRESENT IN A TUBE

FIELD OF THE INVENTION

The present invention relates to apparatus for measuring a property of a fluid present in a tube, with a sensor for measuring the desired property, which sensor is disposed on the tube and is in direct contact with the fluid through a lateral access opening.

BACKGROUND OF THE INVENTION

Various implementations of apparatus for measuring a property of a fluid present in a tube are known. They are utilized in the most diverse apparatus, for example in dialysis monitors, for measuring any properties of the fluid. To this end, they generally comprise a sensor, which is suitable for measuring the desired property. The measured properties of the fluid are, for instance, the temperature, the flow velocity, the pressure, the conductivity, etc.

However, measuring these properties of the fluid requires the sensor to be in direct contact with the fluid, which is generally established through a lateral access opening, i.e. a lateral opening in the tube. For this, the sensor is arranged on the tube in such a way that it protrudes at least partially into the tube through the lateral access opening, and is thus in direct contact with the fluid which flows substantially completely around it. This is necessary for temperature sensors, for example, which must be substantially entirely surrounded by the fluid, or which have the fluid flow substantially entirely around them, in order to record an exact temperature.

The sensor may also be disposed on the tube such that it protrudes only into the lateral access opening, but not into the tube itself, so that it is in contact with the fluid, but the fluid does not flow completely around it, or is not entirely surrounded by fluid. This is adequate, for example, for sensors with electrodes for measuring the inductance of the fluid.

However, owing to the geometry of the tube it is difficult to provide a lateral access opening that, on the one hand, allows for direct contact of the sensor with the fluid and, on the other hand, is reliably sealed from the surroundings. Apart from the requisite direct contact with the fluid, the sensor disposed on the tube also needs a connection to an evaluating unit or the like, in order to relay the measured values.

To resolve the sealing problems, German Patent Publication No. 35 08 570 suggests, for example, inserting a shut-off valve with a plug in a tube, the plug comprising a bore in the axis of rotation. A sensor is inserted in the bore and sealed with a sealing ring. Then, when for example as a result of the composition of the fluid, deposits build up with time on the sensor that is in direct contact with the fluid and impede the exact measurement of the required measured value, it is possible to replace the sensor without difficulty. To this end, the shut-off valve is set in its blocking position so that the fluid flow is interrupted and the sensor can be replaced without loss of fluid.

A disadvantage of this type of apparatus is that the tube must be completely severed during installation of the shut-off valve. Thus, after successful installation of the shut-off valve, additional seal surfaces with additional possible unsealed areas are created. Moreover, a shut-off valve entails an additional material expense in addition to the supplementary installation expense, thus creating additional costs.

An apparatus is known from German Patent Publication No. 41 01 549 for measuring temperatures in tubes, in which a bushing is welded laterally to a tube and forms a lateral access opening. A plug having a central bore is inserted in the bushing. Furthermore, a temperature sensor is screwed into the bushing and is pushed through the bore of the plug to the fluid, and protrudes into the fluid. The plug, which seals the temperature sensor from the fluid, is specifically worked on the side directed towards the fluid. This is intended to prevent the formation of gaps between the plug and the tube wall as breeding grounds for bacteria and other germs.

While this makes possible a reliable seal of the temperature sensor from the fluid, this seal also requires a larger amount of labor. Specifically, lateral access to the tube must be provided, a bushing must be welded to the lateral access or the tube, respectively, and the plug specifically worked on the side directed towards the fluid, before the temperature sensor can be screwed into the bushing. This creates supplementary costs in addition to the required additional material.

An apparatus for measuring the temperature of a fluid present in a tube is known from European Patent No. 413,198, in which a bushing is similarly welded laterally to a tube and forms a lateral access opening to the fluid. An extensively worked ball valve is screwed into the bushing. A temperature sensor is pushed through the ball valve in the latter's open position up to the fluid in the tube, and is sealed against the fluid by ring seals before the ball valve and after the ball valve. In this way it is possible to replace the temperature sensor without shutting off the fluid. However, numerous seal surfaces are necessary, which increases the risk of leaks. In addition, this known apparatus is also expensive in terms of material and labor and is therefore costly.

In view of this background it is therefore an object of the present invention to provide apparatus for measuring a property of a fluid present in a tube, with a sensor for measuring the property, which sensor is arranged on the tube and in direct contact with the fluid through a lateral access opening, that is simple and inexpensive to manufacture and in which the lateral access opening is reliably, simply and inexpensively sealed.

SUMMARY OF THE INVENTION

In accordance with the present invention, this and other objects have now been realized by the discovery of apparatus for measuring a property of a fluid comprising a tube for retaining the fluid, the tube including an outer wall, a lateral access opening, and a domed portion including a sealing surface on the outside wall of the tube surrounding the lateral access opening, and a sensor sealingly disposed on the sealing surface surrounding the lateral access opening in the tube for direct contact with the fluid in the tube for sensing the property of the fluid in the tube. Preferably, the sealing surface comprises a level surface.

In accordance with one embodiment of the apparatus of the present invention, the domed portion of the tube comprises a bend in the entire tube.

In accordance with another embodiment of the apparatus of the present invention, the domed portion of the tube comprises an outward bulge on one side of the tube.

In accordance with another embodiment of the apparatus of the present invention, the sealing surface comprises the wall of the tube.

In accordance with another embodiment of the apparatus of the present invention, the apparatus includes adhering means for adhering the sensor to the sealing surface.

In accordance with another embodiment of the apparatus of the present invention, the sensor is a temperature sensor, a pressure sensor, a flow meter, and/or a conductivity sensor. Preferably, the apparatus includes a leveled-off planar portion of the wall of the tube on the outer side of the domed portion thereby providing the lateral access opening. In a preferred embodiment, the leveled-off planar portion of the wall comprises a ground-off portion thereof.

In accordance with one embodiment of the apparatus of the present invention, the tube is elastic, flexible, or rigid. Preferably, the rigid tube is made from metal, plastic and glass.

In accordance with another embodiment of the apparatus of the present invention, a dialysis monitor is provided including apparatus for measuring a property of a fluid as set forth above.

In accordance with the present invention, the above objects are achieved with apparatus of the type discussed above in which the tube includes a domed wall portion, the domed wall portion includes a seal surface on its outer side, the lateral access opening is formed in the seal surface, and the sensor is disposed in a sealed manner on the seal surface over the lateral access opening.

In this manner, a simple apparatus is provided, which for example may be used in dialysis monitors, which enables a simple and at the same time reliable seal of the lateral access opening on the tube. With the formation of the domed wall portion in the tube and the arrangement of a seal surface on the outer side of this domed wall portion, a large seal surface is provided that is formed substantially without edges and corners, on which the sensor can be simply disposed in a reliably sealed manner. The sensor is arranged over the lateral access opening, which is arranged in such a way in the seal surface, or which terminates in such a way in the seal surface, that it is surrounded by the seal surface. In this manner, on the one hand, the lateral access opening is simply and reliably sealed by the sensor itself and, on the other hand, the sensor is readily brought into direct contact with the fluid. The sensor thus sits on the seal surface and is simultaneously in direct contact with the fluid.

By forming a domed wall portion and arranging a seal surface on the outer side thereof, there is in particular provided a larger seal surface that comprises no edges or corners and on which the sensor can sit. The apparatus known from the prior art having a lateral access opening in the tube generally include lateral seal surfaces having edges, corners or gaps. The sensor lies laterally against these seal surfaces, which renders a reliable seal difficult. This problem is removed by the present invention.

In particular when, in accordance with a preferred embodiment, the seal surface is a level surface, a further improved seal of the lateral access opening is made possible. A reliable seal can be obtained more easily on a level surface, and the sensor can simply be placed on the seal surface so that it covers the lateral access opening. When an appropriate seal is provided between sensor and seal surface, for example a sealing ring or even adhesion between sensor and seal surface, as provided in accordance with another preferred embodiment, the lateral access opening is then reliably sealed by the sensor itself.

The domed wall portion of the tube can be formed in any manner. For example, the whole tube can be bent to form the domed wall surface, as is provided according to a preferred embodiment. Similarly, the wall of the tube can be distended with a bulge on one side to form the domed wall portion, which is provided according to another preferred embodiment.

In both cases care should be taken that an adequately large domed wall portion is available to provide a sufficiently large seal surface on its outer side. Advantageously, in this case the wall of the tube forms the seal surface, which further facilitates the manufacture thereof.

The lateral access to the interior of the tube arranged in the seal surface can be formed in any manner. However, it is advantageous, and provided according to a preferred embodiment, when the lateral access opening is formed by levelling away the wall of the tube at the outer side of the domed wall portion along a flat plane. In doing this it is advantageous when the domed wall portion is ground away at its outer side to form the lateral access opening. In this manner, the seal surface will simultaneously be formed with the lateral access so that the manufacture is further simplified and the arrangement becomes altogether less expensive. Moreover, in this manner, a transition between the lateral access opening and the interior of the tube is provided that is favorable to flow, which is of particular advantage when the fluid present in the tube flows.

The lateral access opening can be formed in the manner described above both with an elastic and/or flexible tube, or also with a rigid tube. This apparatus is, however, particularly advantageous with a rigid tube, that for example can consist of metal, synthetic material or even glass. Particularly in the case of glass the sealing of a lateral access opening was previously difficult and coupled with problems, which are now removed by the present invention.

Any sensors can be used in the arrangement, such as for example temperature sensors, pressure sensors, flow meters or even conductivity sensors. Furthermore, the apparatus can be employed in diverse apparatus, such as in dialysis monitors.

BRIEF DESCRIPTION OF THE DRAWINGS

The present invention will now be described in more detail with reference to the following detailed description, which, in turn, refers to the enclosed drawings, which depict preferred embodiments, as follows.

DETAILED DESCRIPTION

Figure 1:
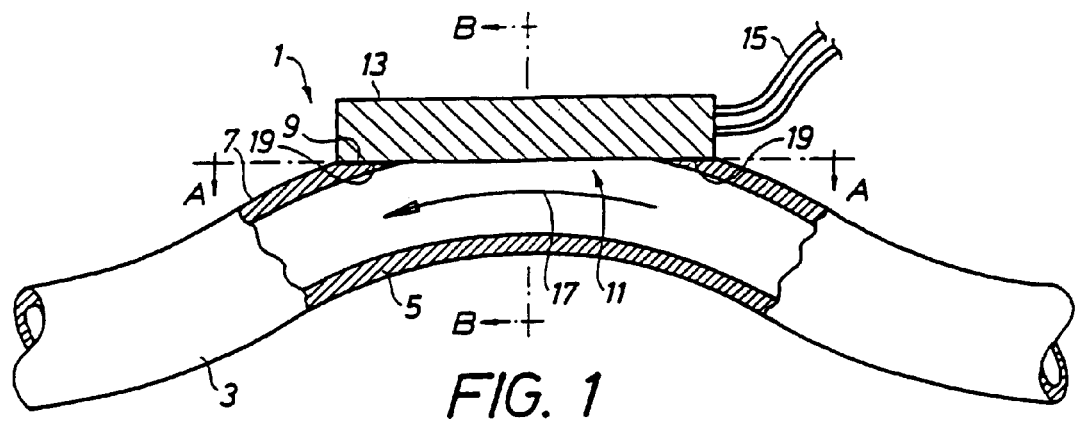
FIG. 1 is a side, elevational, partially sectional view of one embodiment of the apparatus of the present invention.

Referring to the drawings, in which like reference numerals refer to like elements thereof, FIG. 1 shows a first embodiment of the measurement apparatus 1 in longitudinal section. The measurement apparatus 1 includes a sensor 13 that is disposed on a tube 3 to measure properties of a fluid 17 present in the tube 3. The fluid 17 can be either stationary in the tube or flow through it.

The tube 3 comprises a domed wall portion 7 that, in this embodiment, is formed by bending the whole tube 3. On its outer side the domed wall portion 7 there is a seal surface 9, in which a lateral access opening 11 is arranged. In this embodiment, the seal surface 9 is formed together with the lateral access opening 11 by grinding away the outer side of the domed wall portion 7 along a flat plane. This plane is indicated by the dashed and dotted line A—A. The seal surface is thus formed by the ground away portion of the wall 5 of the tube 3. The form of the transition between the lateral access opening 11 and the interior of the tube 3 that is very favorable in fluid mechanical terms can be readily seen here, and is particularly advantageous when the fluid flows.

The sensor 13 is arranged on the seal surface 9 in such a manner that it completely covers and thus seals the lateral access opening 11. Simultaneously, it is in direct contact with the fluid 17. The required seal between sensor 13 and seal surface 9 can be achieved in any desired manner. In the embodiment illustrated here, the sensor 13 is glued on the seal surface 9 by means of a suitable adhesive 19. However, it is also possible to provide, for example, a sealing ring or any other seal between the sensor 13 and the seal surface 9, whereby the sensor can then be attached to the tube 3 with any other suitable means.

The tube 3 in this case consists of glass but may consist of any other material such as plastic, metal or an elastic material.

In the first embodiment of the measurement apparatus 1 shown here the sensor 13 is in direct contact with the fluid 17 present in the tube 3 through the lateral access opening 11 of the tube 3. In this manner, the sensor 13 can directly determine or measure the desired property of the fluid 17 and relay the measured values by means of electrical connections 15 to an evaluation unit or the like, which is not illustrated, where they can then be processed.

Figure 2:
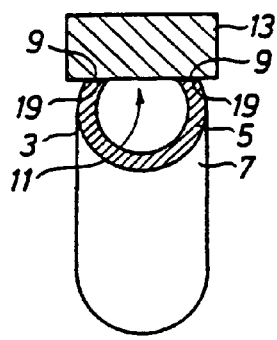
FIG. 2 is a front, elevational, cross-sectional view, taken along line B—B in FIG. 1.

In FIG. 2 is shown a section along line B—B of FIG. 1. As can be readily seen, the seal surface 9 is formed by the wall 5 of the tube 3 that has been levelled away along a flat plane on the outer side of the domed wall portion 7. As mentioned above, in this way the lateral access opening 11 to the interior of the tube 3 is formed at the same time as the seal surface 9, and a transition between the lateral access opening 11 and the interior of the tube 3 is obtained in a fluid-mechanically favorable fashion. The sensor 13 is arranged on the seal surface 9 above the lateral access opening 11 in such a manner that it completely covers, and therefore seals, the lateral access opening 11.

Figure 3:
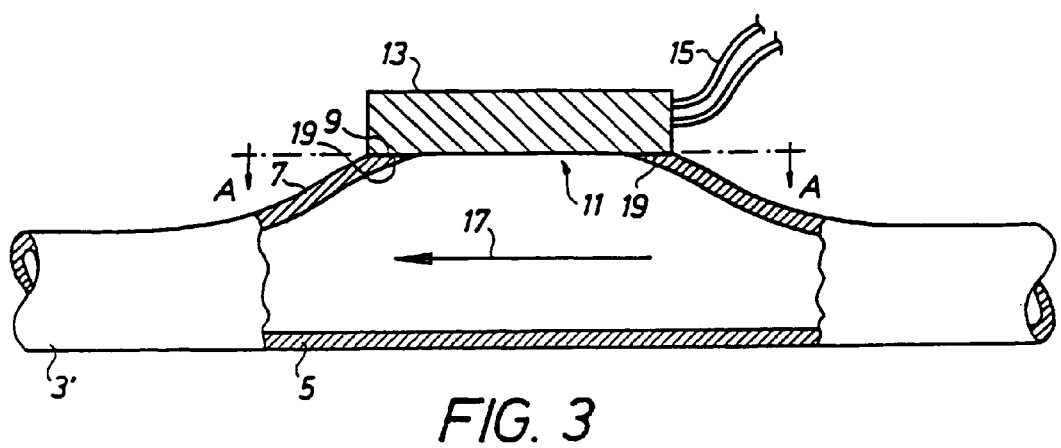
FIG. 3 is a side, elevational, partially sectional view of another embodiment of the apparatus of the present invention.

In FIG. 3 is shown a second embodiment of the measurement apparatus in longitudinal section. Like parts are denoted by like reference numerals. The tube 3' of this embodiment is not bent as a whole to form the domed wall portion 7. Instead, only a region of the wall of the tube 3' bulges outwardly to form the domed wall portion 7.

Furthermore, in this case a seal surface 9 that is created by levelling away the outer side of the domed wall surface along a straight line A—A is formed on the outer side of the domed wall portion 7. As mentioned, in this manner the lateral access opening 11 is formed at the same time. The sensor 13 is then, in turn, arranged on the seal surface 9 such that it completely covers, and accordingly seals, the lateral access opening 11, while being simultaneously in direct contact with the fluid 17. A seal between sensor 13 and seal surface 9 is accomplished in this embodiment also by gluing the sensor 13 to the seal surface 9 by means of a suitable adhesive 19. The tube 3' is of metal, however the embodiment shown here can also be utilized with tubes of any other material, such as for example glass or plastic, or even elastic materials.

Here again the sensor 13 is coupled by electrical connections 15 to an evaluating unit (not shown), or the like, in order to relay and process the values determined by the sensor 13 regarding the property of the fluid 17 present in the tube 3'.

In the embodiment shown in FIG. 3 the cross-section of the tube 3' expands in the region of the apparatus, while the cross-section of the tube 3 of the first embodiment shown in FIG. 1 narrows in the region of the apparatus. Thus, the flow velocity of a fluid 17 flowing in the apparatus according to the first embodiment increases, while the flow velocity of a fluid 17 flowing in the arrangement according to the second embodiment decreases. This can influence the property of the fluid 17 to be measured so that, depending on the property of the fluid 17 to be measured, the embodiment that does not, or least, influences the property to be measured is to be selected. Alternatively, however, it is also possible to form the domed wall portion 7 on the tube 3 or 3' such that no change, or only an extremely small and negligible change in cross-section of the tube 3 or 3', results.

Figure 4:
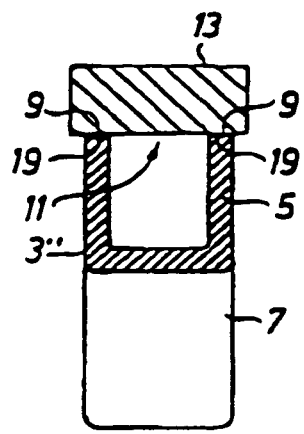
FIG. 4 is a front, elevational, cross-sectional view of yet another embodiment of the apparatus of the present invention.

An example of this is shown in FIG. 4, which shows a cross-section through the tube 3" in a similar fashion to FIG. 2. Like parts are denoted by like reference numerals. The tube 3" is rectangular and bent as a whole to form the domed portion 7 in a similar fashion to that shown in FIG. 1. The outer side of the domed portion 7 is completely levelled away up to the side walls to form the lateral access opening 11, such that the sensor 13 placed thereon takes the place of the original outer side. In this way, the original cross-section is retained.

Figure 5:
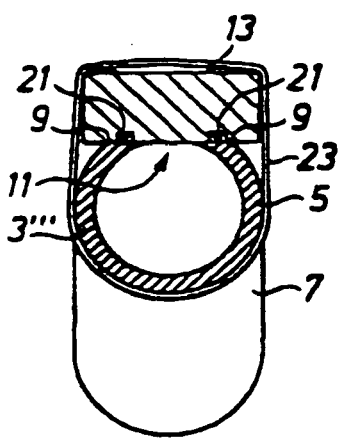
FIG. 5 is a front, elevational, cross-sectional view of yet another embodiment of the apparatus of the present invention.

A further example is shown in FIG. 5, which likewise shows a cross-section through a tube 3''' in a similar fashion to FIG. 2. Here again, like parts are denoted by like reference numerals. The tube 3''' comprises a circular cross-section and is bent as a whole to form the domed portion 7, in a similar fashion to that shown in FIG. 1. To form the lateral access opening 11, the outer side of the domed portion 7 is levelled away to just such an extent that a small opening is formed in the wall 5. This is covered by the sensor 13 placed thereon, the sensor 13 protruding only a little into the tube 3'''. This has the effect that the cross-section of the tube in the region of the measurement apparatus is only slightly, and on the whole negligibly, reduced.

Contrary to the previous embodiments, the sensor 13 is in this case attached to the seal surface 9 with a holding band 23. The seal between sensor 13 and tube 3, or seal surface 9 respectively, is obtained with a sealing ring 21 in this embodiment.

Figure 6:
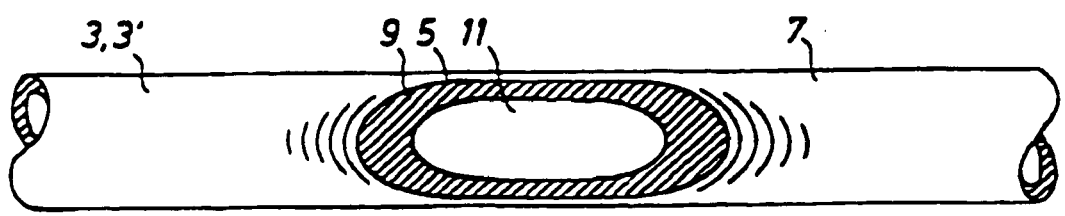
FIG. 6 is a top, elevational view taken along line A—A in FIG. 1 and FIG. 3.

FIG. 6 shows a plan view of a section along the line A—A in FIG. 1 and FIG. 3. It can be clearly seen here that the lateral access opening 11 is arranged in the seal surface 9 such that it is completely surrounded by the seal surface 9. This enables the simple, safe and reliable seal between the lateral access opening 11 and the sensor 13 (not shown), as described in detail above. The seal surface 9 is formed by the levelling away of wall 5 of the tube 3, 3' along a flat plane, which enables its simple and inexpensive formation. Moreover, in this manner, a level seal surface is provided that comprises no corners, edges or gaps and thus enables a simple and reliable seal.

Hence, an apparatus for measuring a property of a fluid present in a tube is provided that is simple and inexpensive to manufacture and simply and inexpensively enables a reliable sealing of the sensor utilized in the apparatus. The apparatus can be employed for any application and for any apparatus, for example also in dialysis monitors. In the latter, the apparatus could, for example, be equipped with a conductivity sensor to determine the conductivity of the dialysis fluid. However, this does not limit the apparatus to this purpose.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. Apparatus for measuring a property of a liquid comprising a tube for retaining said liquid, said tube including an outer wall, a lateral access opening in said outer wall, and a domed portion including a sealing surface on said outer wall of said tube surrounding said lateral access opening, and a sensor sealingly disposed on said sealing surface surrounding said lateral access opening in said tube for sealing said sealing surface and for direct contact with said liquid in said tube for sensing said property of said liquid in said tube.

2. The apparatus of claim 1 wherein said sealing surface comprises a level surface.

3. The apparatus of claim 1 wherein said domed portion of said tube comprises a bend in said entire tube.

4. The apparatus of claim 1 wherein said domed portion of said tube comprises an outward bulge on one side of said tube.

5. The apparatus of claim 1 wherein said sealing surface comprises the wall of said tube.

6. The apparatus of claim 1 including adhering means for adhering said sensor to said sealing surface.

7. The apparatus of claim 1 wherein said sensor comprises a sensor selected from the group consisting of a temperature sensor, a pressure sensor, a flow meter, and a conductivity sensor.

8. The apparatus of claim 2 including a leveled-off planar portion of said wall of said tube on said outer side of said domed portion thereby providing said lateral access opening.

9. The apparatus of claim 8 wherein said leveled-off planar portion of said wall comprises a ground-off portion thereof.

10. The apparatus of claim 1 wherein said tube is elastic.

11. The apparatus of claim 1 wherein said tube is flexible.

12. The apparatus of claim 1 wherein said tube is rigid.

13. The apparatus of claim 12 wherein said tube comprises a material selected from the group consisting of metal, plastic and glass.

14. A dialysis monitor including apparatus for measuring a property of a liquid as set forth in claim 1.

15. Apparatus for measuring a property of a liquid comprising a tube for retaining said liquid, said tube including an outer wall, a lateral access opening in said outer wall, and a domed portion including a sealing surface on said outer wall of said tube surrounding said lateral access opening, and a sensor in direct contact with said lateral access opening for sealing said sealing surface and for direct contact with said liquid in said tube for sensing said property of said liquid in said tube.

16. The apparatus of claim 1 wherein said sealing surface comprises a cut-away portion of said domed portion of said tube providing a substantially flat sealing surface on said outer wall of said tube.

17. The apparatus of claim 1 wherein said sensor does not extend within said tube in a manner to significantly reduce the cross-sectional area of said tube.

18. The apparatus of claim 16 wherein said sealing surface comprises a cut-away portion of said domed portion of said tube providing a substantially flat sealing surface on said outer wall of said tube.

19. The apparatus of claim 17 wherein said sensor does not extend within said tube in a manner to significantly reduce the cross-sectional area of said tube.

* * * * *

UNITED STATES PATENT AND TRADEMARK OFFICE
CERTIFICATE OF CORRECTION

| | | |
|---|---|---|
| PATENT NO. | : 7,168,334 B1 | Page 1 of 1 |
| APPLICATION NO. | : 09/980066 | |
| DATED | : January 30, 2007 | |
| INVENTOR(S) | : Johan Drott | |

It is certified that error appears in the above-identified patent and that said Letters Patent is hereby corrected as shown below:

On the Title Page item (74), "Krumholtz" should read --Krumholz--.

Column 1, line 4, insert --CROSS-REFERENCE TO RELATED APPLICATIONS

This application is a continuation of International Application No.PCT/SE00/01132, filed on May 30, 2000, which claims priority to Swedish Application No. 9901981-2, filed on May 31, 1999, the contents of both of which are incorporated herein in their entirety by reference.--

Signed and Sealed this

First Day of May, 2007

JON W. DUDAS
*Director of the United States Patent and Trademark Office*